United States Patent
Lange et al.

(10) Patent No.: US 11,471,108 B2
(45) Date of Patent: Oct. 18, 2022

(54) DEVICE FOR DRAINAGE OF THE BRAIN

(71) Applicant: IPTA GmbH, Waiblingen (DE)

(72) Inventors: Gero Lange, Waiblingen (DE); Heinz Eder, Stuttgart (DE); Christian Roederer, Remshalden (DE)

(73) Assignee: SNP—SMART NEURO PRODUCTS GMBH

(*) Notice: Subject to any disclaimer, the term of this patent is extended or adjusted under 35 U.S.C. 154(b) by 481 days.

(21) Appl. No.: 16/488,420

(22) PCT Filed: Feb. 21, 2018

(86) PCT No.: PCT/EP2018/054316
§ 371 (c)(1),
(2) Date: Aug. 23, 2019

(87) PCT Pub. No.: WO2018/153943
PCT Pub. Date: Aug. 30, 2018

(65) Prior Publication Data
US 2020/0069254 A1    Mar. 5, 2020

(30) Foreign Application Priority Data
Feb. 24, 2017  (EP) .................................... 17157971

(51) Int. Cl.
*A61B 5/00*     (2006.01)
*A61B 5/01*     (2006.01)
(Continued)

(52) U.S. Cl.
CPC .............. *A61B 5/6868* (2013.01); *A61B 5/01* (2013.01); *A61B 5/031* (2013.01);
(Continued)

(58) Field of Classification Search
None
See application file for complete search history.

(56) References Cited

U.S. PATENT DOCUMENTS 4,106,510 A * 8/1978 Hakim ................ A61M 27/006
                                                   604/9
4,787,886 A * 11/1988 Cosman .............. A61M 27/006
                                                   604/9
(Continued)

FOREIGN PATENT DOCUMENTS

EP    0589862 A2    3/1994
EP    1702641 A2    9/2006

OTHER PUBLICATIONS

International Search Report issued in International Application No. PCT/EP2018/054316, dated May 25, 2018, 6 pages.

*Primary Examiner* — Carl H Layno
*Assistant Examiner* — Manolis Pahakis
(74) *Attorney, Agent, or Firm* — Quarles & Brady LLP (57) ABSTRACT

Brain drainage device having a rod-shaped hollow body with an inner drainage channel for insertion through the cranium into the brain, a first sensor arrangement with at least one sensor for measuring a physical parameter, and a signal interface; wherein the rod-shaped hollow body has a first region A which, in the applied state, is designed to protrude into the ventricle situated in the brain; wherein the rod-shaped hollow body has a second region B, which is arranged proximally from the first region, wherein the second region is designed to lie in the region of the brain mass in the applied state; wherein the first sensor arrangement is arranged in the second region in order to measure a physical parameter of the brain mass; wherein the first sensor arrangement is connected to the signal interface such that measurement data determined by the first sensor arrangement are transmitted to a measuring system that is to be connected.

13 Claims, 5 Drawing Sheets

(51) Int. Cl.
  *A61B 5/03* (2006.01)
  *A61B 5/1455* (2006.01)
  *A61M 27/00* (2006.01)
  *A61B 5/291* (2021.01)

(52) U.S. Cl.
  CPC ......... *A61B 5/14551* (2013.01); *A61B 5/291* (2021.01); *A61B 5/6864* (2013.01); *A61M 27/006* (2013.01); *A61B 2562/12* (2013.01)

(56) References Cited

U.S. PATENT DOCUMENTS

| | | | | |
|---|---|---|---|---|
| 5,795,307 | A * | 8/1998 | Krueger | A61B 5/031 604/9 |
| 6,533,733 | B1 * | 3/2003 | Ericson | A61M 27/006 600/128 |
| 10,315,013 | B2 * | 6/2019 | Purdy | A61M 25/09 |
| 2002/0052563 | A1 * | 5/2002 | Penn | A61N 1/36557 600/561 |
| 2003/0139699 | A1 * | 7/2003 | Rosenberg | A61M 27/006 604/9 |
| 2004/0147871 | A1 * | 7/2004 | Burnett | A61M 1/28 604/9 |
| 2004/0243145 | A1 * | 12/2004 | Bobo, Sr. | A61B 5/031 606/129 |
| 2005/0020962 | A1 * | 1/2005 | Reich | A61M 27/006 604/8 |
| 2005/0055009 | A1 * | 3/2005 | Rosenberg | A61B 5/031 604/500 |
| 2005/0070458 | A1 * | 3/2005 | John | A61B 5/369 600/378 |
| 2006/0211946 | A1 * | 9/2006 | Mauge | A61B 5/031 600/488 |
| 2007/0208293 | A1 * | 9/2007 | Mansour | A61B 5/031 604/9 |
| 2008/0146990 | A1 * | 6/2008 | Jenson | A61B 5/03 604/28 |
| 2009/0204019 | A1 * | 8/2009 | Ginggen | A61M 27/006 600/561 |
| 2010/0022896 | A1 * | 1/2010 | Yadav | A61B 5/6846 604/9 |
| 2010/0168532 | A1 * | 7/2010 | Waziri | A61B 5/031 600/301 |
| 2010/0210958 | A1 * | 8/2010 | Manwaring | A61B 5/0538 600/506 |
| 2010/0234792 | A1 * | 9/2010 | Dacey, Jr. | A61B 5/0084 604/8 |
| 2011/0066072 | A1 * | 3/2011 | Kawoos | A61B 5/031 600/561 |
| 2012/0095383 | A1 * | 4/2012 | Radojicic | A61L 31/005 604/8 |
| 2012/0226215 | A1 * | 9/2012 | Hsu | A61M 27/006 604/9 |
| 2012/0271168 | A1 * | 10/2012 | Radojicic | A61M 5/1723 600/439 |
| 2012/0302938 | A1 | 11/2012 | Browd | |
| 2012/0302995 | A1 * | 11/2012 | Hochareon | A61M 1/3604 604/508 |
| 2014/0207043 | A1 * | 7/2014 | Anand | A61M 25/0108 604/8 |
| 2014/0276660 | A1 | 9/2014 | Eckermann | |
| 2014/0316373 | A1 * | 10/2014 | Dhall | A61F 7/12 604/506 |
| 2015/0112289 | A1 * | 4/2015 | Stebbins | A61M 1/70 604/327 |
| 2015/0297874 | A1 * | 10/2015 | East | A61M 27/006 604/9 |
| 2016/0287111 | A1 | 10/2016 | Jacobsen | |
| 2017/0027458 | A1 * | 2/2017 | Glover | A61B 5/028 |
| 2017/0095649 | A1 * | 4/2017 | Vase | A61F 7/123 |
| 2017/0136221 | A1 * | 5/2017 | Budgett | A61M 27/006 |
| 2017/0325685 | A1 * | 11/2017 | Shachar | A61B 5/031 |
| 2018/0000421 | A1 * | 1/2018 | Kim | A61B 5/686 |
| 2020/0001058 | A1 * | 1/2020 | Miethke | A61M 27/006 |
| 2020/0022587 | A1 * | 1/2020 | Glover | A61B 5/4255 |
| 2020/0170542 | A1 * | 6/2020 | Waziri | A61B 5/24 |
| 2021/0213260 | A1 * | 7/2021 | Luciano | A61B 5/6852 |

* cited by examiner

DEVICE FOR DRAINAGE OF THE BRAIN

CROSS-REFERENCE TO RELATED PATENT APPLICATION

This application is a U.S. national stage entry of International Application PCT/EP2018/054316, filed Feb. 21, 2018, which claims priority to European Application 17157971.7, filed Feb. 24, 2017.

TECHNICAL AREA

The invention relates to a device for drainage of the brain, in particular a device for drainage of the brain with an integrated sensor arrangement for monitoring physical parameters, specifically the cerebral pressure during a procedure.

BACKGROUND OF THE INVENTION

Cerebral pressure is a colloquial term for the pressure that prevails inside the skull (intracranial pressure, commonly abbreviated as ICP in the medical field). The intracranial pressure is crucial for the circulation and thus for the functioning of the brain as it counteracts the pressure with which blood is pumped into the brain. If the intracranial pressure and mean arterial blood pressure are the same, the brain will no longer be supplied with blood. The brain will reduce its activity quickly and die within a short period of time. Therefore, the measurement of intracranial pressure is an important guide to therapeutic decisions in the treatment of patients with severe brain damage, for example, following a traumatic brain injury or a stroke.

Measurements of the intracranial pressure are used, for example, in the area of postoperative tumour after-care, traumatic brain injury, parenchymatous and intraventricular cerebral haemorrhage and stroke. Increased intracranial pressure can, for example, lead to congestion papillae, headache and vomiting.

Conventional methods used to measure intracranial pressure are either non-invasive and thus offer a certain patient comfort with the respective measurement accuracy or invasive with a higher measurement of accuracy but significantly lower patient comfort.

The liquor cerebrospinalis (cerebrospinal fluid, CSF) is a clear and colourless body fluid that is associated with the tissue fluid of the brain and is therefore very similar in its composition. The cerebrospinal fluid is squeezed out of the blood into the choroid plexus, mainly in the lateral ventricles (but also in parts of the third and fourth ventricles), enters the fourth ventricle via the third ventricle and the mesencephalic aqueduct, and from there the external CSF passes through openings in the external cerebrospinal fluid space outside the brain. At this point, the resorption of cerebral water takes place in venous blood vessels. It is therefore a circulating system.

If the CSF production is too high or if the CSF cannot drain properly because a tumour, cerebral haemorrhage or other swelling impairs drainage, this leads to the development of an internal hydrocephalus, a stasis of the cerebral water in the ventricular system. This can put pressure on the brain (intracranial pressure), which can be life-threatening. To avert this danger to life, the pressure must be discharged from the ventricle. To this purpose, a tube or thin needle (Duisburg needle) is inserted into the ventricular system from the outside through the cranium in a small procedure that can be performed either in the operating room or bedside in the intensive care unit. Due to this discharge, the CFS can then escape, and the danger is temporarily averted.

Because such external ventricular drainage is a potential gateway for germs, it cannot remain there indefinitely. It is, therefore, only suitable as a temporary discharge. If a permanent CSF discharge is required, a so-called internal cerebral shunt, for example in the form of a ventriculoperitoneal shunt, must be placed surgically.

SUMMARY OF THE INVENTION

The present invention provides an improved device for drainage of the brain according to the independent claims, in particular a device for drainage of the brain with an integrated sensor arrangement, specifically for the measurement of intracranial pressure. Advantageous embodiments and further developments are provided in the dependent claims and the description below.

According to one embodiment of the invention, a device for drainage of the brain is proposed with a rod-shaped hollow body with an inner drainage channel for insertion through the cranium into the brain, a first sensor arrangement with at least one sensor for measuring a physical parameter and a signal interface; wherein the rod-shaped hollow body has a first region which, in the applied state, is designed to protrude into the ventricle situated in the brain; wherein the rod-shaped hollow body has a second region, which is arranged proximally from the first region, wherein the second region is designed to lie in the region of the brain mass in the applied state; wherein the first region has a drainage opening arrangement connected to the drainage channel, via which liquor can be drained from the ventricle into the drainage channel in the applied state; wherein the first sensor arrangement is situated in the second region to measure a physical parameter of the brain mass; wherein the first sensor arrangement is connected to the signal interface such that measurement data determined by the first sensor arrangement are transmitted to a measuring system that is to be connected. In this way, the ventricle can be drained in a gentle and reliable manner while the relevant physical parameters that are the expression of the medical condition of the patient can be monitored at the same time.

In one embodiment of the invention, the first sensor arrangement essentially has a geometry-constant shape. In other words, the sensor arrangement and the measurement process have no influence on the geometry of the device for drainage of the brain. In this way, an effect of the sensors and the device for drainage of the brain on the patient's body can be reduced.

According to one embodiment of the invention, the device for drainage of the brain may comprise a plurality of sensors which are connected to a measuring system to be connected. The plurality of sensors can measure different physical parameters, for example. The sensors may be joined in a structural unit and thus combined. Sensors for temperature, blood oxygen saturation, intracranial pressure measurement and/or brain activity may be combined in a sensor arrangement. The sensor arrangement may be applied externally to the hollow body. It is possible to apply the sensor arrangement for measuring, for example, intracranial pressure, temperature, oxygen and/or brain activity (EEG) with a printing method, for example, a galvanic, lithographic or jet printing method. The sensor arrangement can also be placed on the inside through the hollow body. The sensor arrangement may comprise a plurality of sensors of the same or different types. The sensors may be provided at different positions and/or with different measurement angles. The sensors may be embedded in recesses on the outside of the rod-shaped hollow body so that they are flush with the outside of the hollow body and do not protrude.

According to one embodiment of the invention, the hollow body of the device for drainage of the brain may be made of a titanium alloy or titanium. The hollow body that accommodates the measuring sensor may consist of a non-magnetic, radiation-permeable material. The material may be metallic, in particular titanium or a titanium alloy or plastic. The advantages of a metallic material are seen in the fact that the length is easier to calibrate compared to plastic. The hollow body may be coated with a plastic. The hollow body may be capable of being sterilised and in particular may be capable of being sterilised by heat.

According to one embodiment, the hollow body may, for example, have a minimum diameter of 1 mm, and its maximum diameter may be around 10 mm, for example.

In one embodiment, the device for drainage of the brain may have a plurality or only one drainage opening. According to one embodiment, the rod-shaped hollow body may comprise the drainage openings exclusively on the cylindrical parts so that the frontal area is designed without an opening. This reduces the risk of injury when inserting the rod-shaped hollow body into the cranium or the cerebral mass of the patient. Alternatively, a single drainage opening may be an opening of a through bore extending along the longitudinal axis of the hollow body at the end of the hollow body. The drainage openings may be oval or elliptical and may be rounded at the edges to the outside of the hollow body to avoid injury.

According to one embodiment of the invention, the device for drainage of the brain may comprise a second sensor arrangement in the first region with the drainage opening arrangement having at least one sensor selected from the group consisting of: Oxygen content sensor, oxygen saturation sensor, pressure sensor and temperature sensor to determine a corresponding physical parameter in the ventricle as well. The second sensor arrangement may also be connected to the signal interface to transmit measured data determined by the second sensor arrangement to a measuring system to be connected. In this way, physical parameters may be determined and read in the ventricle region as well.

According to one embodiment of the invention, at least one sensor of the first and/or second sensor arrangement comprises a sensor for detecting an oxygen content in the region of the cerebral mass or the ventricle with at least one light source for light having at least a first wavelength and a second wavelength, and at least one first light sensor associated with the light source and sensitive to the first wavelength, and a second light sensor associated with the light source and sensitive to the second wavelength. The first and the second light sensor may also be combined in a structural unit. According to one embodiment, the light source and the associated light sensors may be arranged so that they are axially and/or azimuthally spaced from each other.

In this way, the oxygen saturation may be determined on the basis of two different wavelengths of light, which are, for example, in the range of the red or infrared light, i.e. for example, at a wavelength greater than 570 nm or 600 nm.

According to one embodiment of the invention, the device for drainage of the brain comprises a controllable valve arrangement in the drainage channel proximal to the drainage opening arrangement so as to be able to open and close the drainage channel in a targeted manner. This may be done either by means of a threshold pressure, which can be set on the valve, or depending on a pressure measured by one of the sensor arrangements. For this purpose, the measuring system may have an adjustable control circuit via which the valve arrangement can be automatically controlled in order to maintain a preset pressure.

According to one embodiment, the controllable valve arrangement has a valve seat connected to an inner wall of the drainage channel and a valve element which is displaceable with respect to the drainage channel and sealed relative to the valve seat. This valve element be moved, for example, by a piezoelectric element. The valve element may be aerodynamically optimised and, for example, have an ellipsoidal shape or projectile shape.

According to one embodiment of the invention, a portion of the inner wall of the drainage channel, the valve seat and the valve element may be formed as a preassembled or prefabricated unit, which is inserted into the rod-shaped hollow body during the production of the device for drainage of the brain. For this purpose, an offset or recess may be provided in the rod-shaped hollow body in the drainage channel so that the prefabricated unit forms an aligned inner wall of the drainage channel together with the main body of the rod-shaped hollow body in the assembled state.

According to one embodiment of the invention, the rod-shaped hollow body may have markings for, for example, the penetration depth, which can be applied very precisely, for example, by means of a laser or an etching method. The hollow body may have a curved surface at its free distal end to push cerebral mass aside.

According to one embodiment of the invention, the distal region of the rod-shaped hollow body may have a thickening produced, for example, by pushing a ball with a through bore onto the rod-shaped hollow body and connecting it firmly and without gaps. In this way, the cerebral mass can be gently pushed aside as the device for drainage of the brain is inserted.

The term distal refers to an area in the direction of the human body or the middle of the body, in this case the area with drainage openings. The term proximal refers to an area in a direction away from the human body.

Magnetically inactive material is understood to be material that is essentially neutral in magnetic field-based examination methods and does not develop significant magnetic properties. This is done to avoid interfering artifacts in imaging techniques, such as MRIs. Such materials may be, for example, titanium or titanium alloys or plastics. Titanium has the advantage that it can be thermally sterilised. Plastics are easy to work with.

The geometry-constant form is understood to refer to a shape that does not significantly change its geometric shape. A pressure sensor with a pressure membrane does not significantly alter the shape of the device for drainage of the brain. By contrast, a balloon catheter, in particular when used for pressure measurements, changes its shape and occupies space. However, this is not always desirable for brain applications, especially elevated cerebral pressures, as it can lead to unpredictable pressure loads.

The attachment to the cranium may be done directly or indirectly, for example, by using a cutting screw in which the rod-shaped hollow body is fixed or is able to be fixed.

The printed signal connection or even sensors may be printed circuit conductor paths or electrodes and insulating layers, for example. They could also be produced in multi-layer technology. Production processes such as galvanic deposition, chemical modification and/or etching techniques as used in production of semiconductors, lithography processes or jet processes analogously to an inkjet printer are comprised here as well. The conductor paths usually face each other and are provided with an outside insulating layer. The outer insulating layer may also be provided by the coating of the entire rod-shaped hollow body. This coating may be provided, for example, by a powder coating. Insulation layers, both for the conductor paths as well as for the sensors, such as for insulation from the rod-shaped hollow body, may also be applied by using sputtering technology, for example, by sputtering glass, which is specified so that it neither splinters nor breaks.

BRIEF DESCRIPTION OF THE DRAWINGS

The invention will be explained and clarified with reference to the following drawings.

Further features, advantages and possible applications of the present invention are provided in the following description of exemplary embodiments and the figures. All described and/or illustrated features alone and in any combination form the subject matter of the invention regardless of their composition in the individual claims or their back references. In the figures, like reference numerals represent like or similar objects.

DETAILED DESCRIPTION OF EXEMPLARY EMBODIMENTS

The present invention provides for a measurement directly on a probe of a device for drainage of the brain. In addition, the invention provides, inter alia, for the combination of several measurement methods (e.g. ICP (intracranial pressure measurement) via a probe, pressure measurement of the cerebral blood flow and measurement of brain activity, temperature, etc.) and the integration of ICP, blood flow measurement and brain activity in one device. Conventionally, such measuring methods take place independently of each other, and there is no aggregated data base from these measurements. Furthermore, known measuring methods suffer from the fact that the inaccuracy of the pressure measurement increases as the ICP becomes higher.

Figure 1:
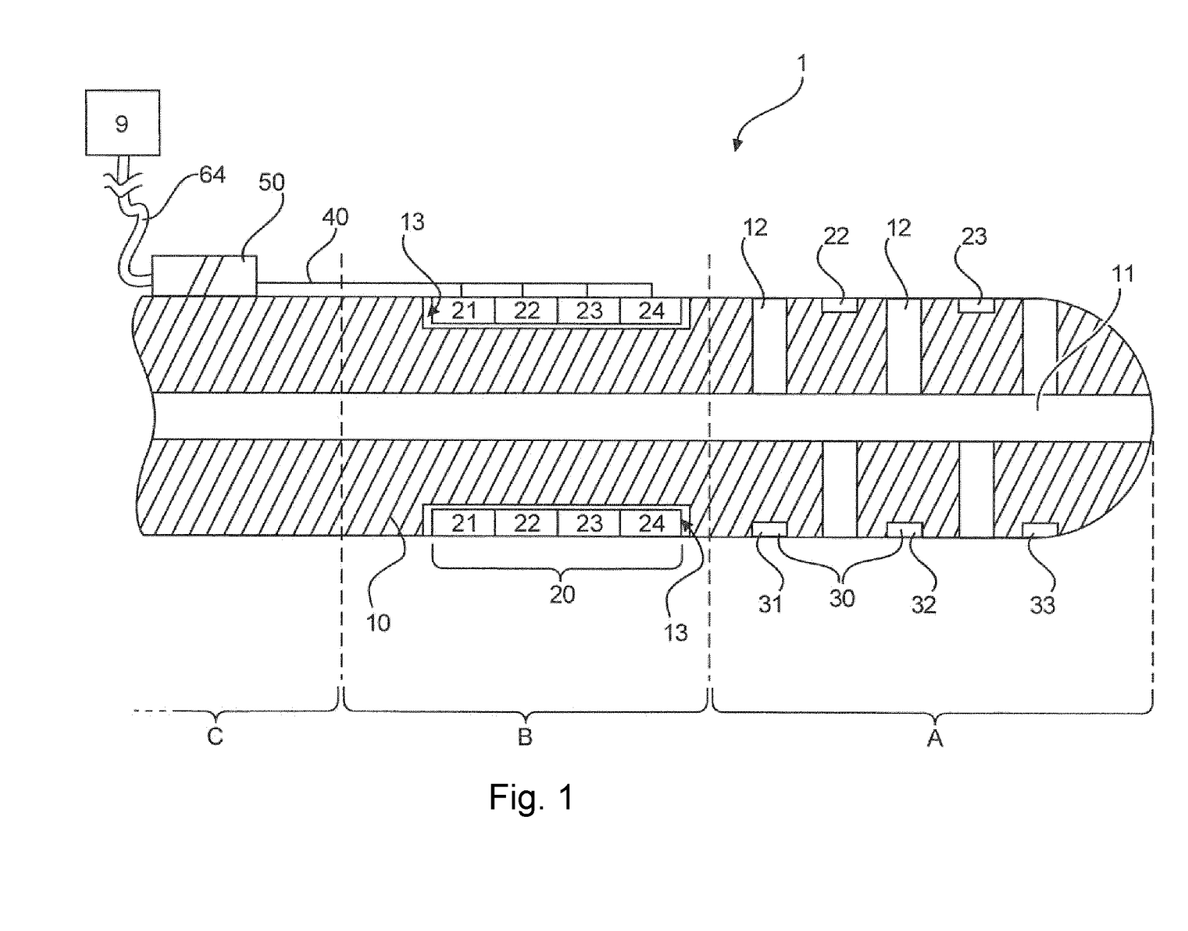
FIG. 1 shows a sectional view of an arrangement according to the invention (not to scale).
Figure 2:
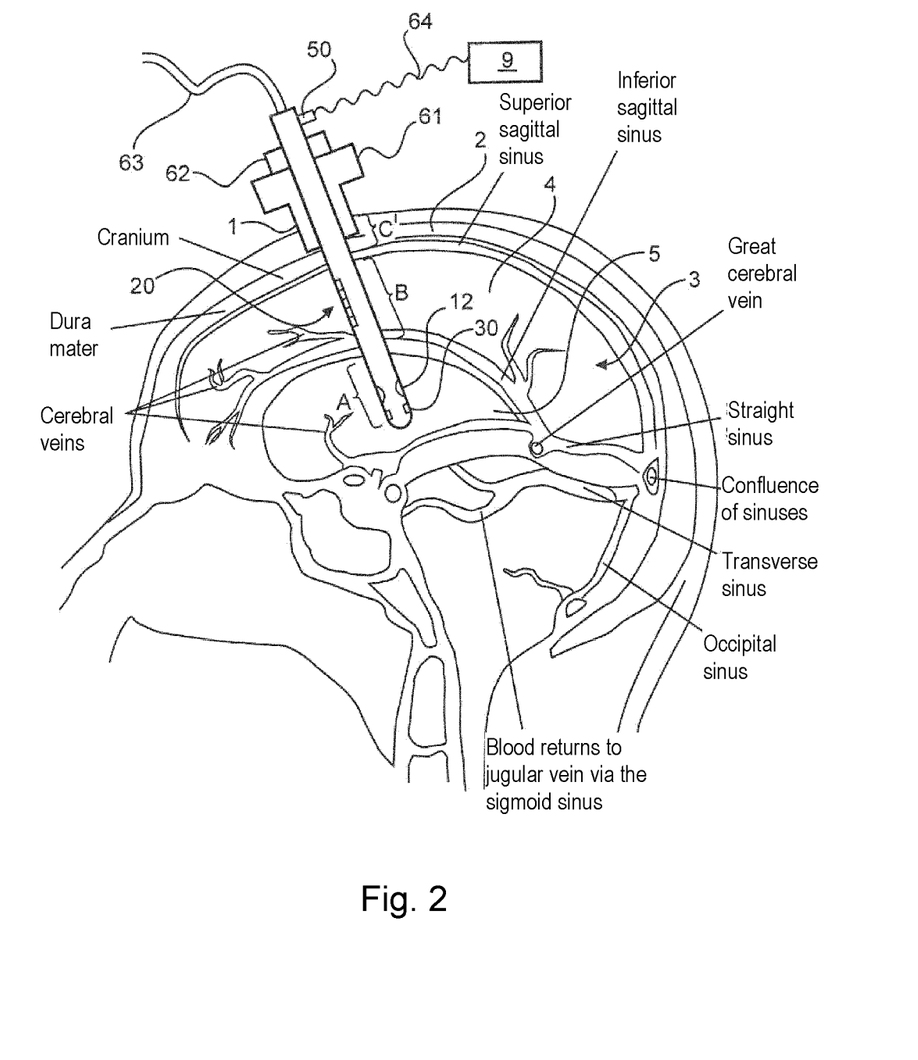
FIG. 2 shows a possible application of the arrangement according to the invention to the human anatomy.
Figure 5:
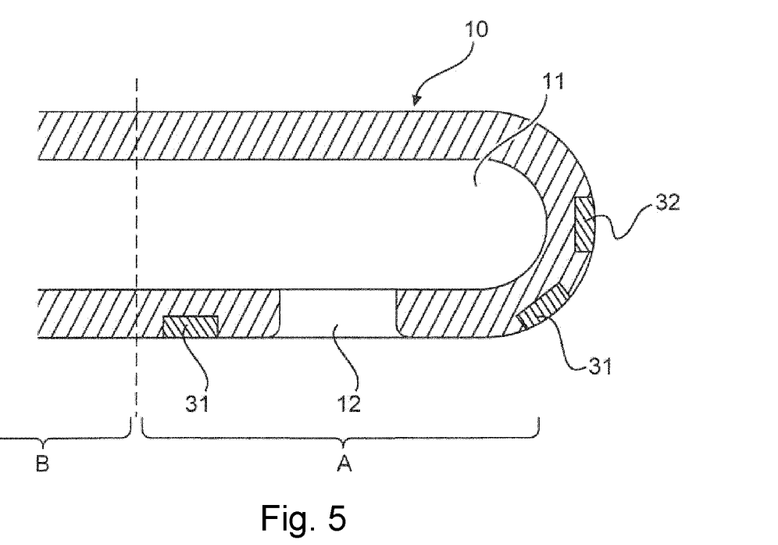
FIG. 5 shows an embodiment of the tip section or ventricle region according to one embodiment of the invention.

FIG. 1 shows an exemplary embodiment of the invention wherein the device for drainage of the brain 1 is shown in a cross-sectional view. The device for drainage of the brain has, for example, three regions: A, B, C. As can be seen in FIG. 2, the region A is in the ventricle 5 of the brain in the applied state. Region B is situated in the area of the brain mass while region C is in the area of the skullcap or outside of the cranium. The device for drainage of the brain 1 has a rod-shaped hollow body 10 in which an inner drainage channel is provided. Drainage openings 12 are provided in the rod-shaped hollow body 10, which connect the drainage channel 11 with the outside of the rod-shaped hollow body 10. The drainage openings 12 may either be provided only on the cylindrical part of region A so that the frontal area remains essentially integrally closed, as shown in FIG. 5, or they may also be provided on the frontal area, as shown in FIG. 1. In region B, which lies in the area of the cerebral mass, a sensor arrangement 20 may be provided, which, in turn, may have a plurality of different individual sensors, which, however, may be combined into the sensor arrangement 20. The sensors 21, 22, 23, 24 may be pressure sensors, temperature sensors, brain activity sensors or oxygen saturation sensors. The sensors or the sensor arrangement 20 may be inserted into a corresponding recess 13 on the outside of the rod-shaped hollow body 10 so that the sensors 20 do not protrude beyond the outside of the rod-shaped hollow body 10. In this way, an integral surface may be created which may reduce the risk of injury or unwanted deformations during application. The gap between the sensors 21, 22, 23, 24 and the rod-shaped hollow body may be provided with an insulating layer. This may be, for example, a polymeric insulating material or glass. In the installed state, the sensors may also be provided with a coating which may also protrude beyond the remaining outside of the rod-shaped hollow body 10 in order to close gaps. The sensors may be connected by means of a signal connection 40 to a signal interface 50, wherein the signal interface lies substantially outside the actual cranial region, here in the region C. The connection between the sensors and the signal interface 50 may be established by a printed signal line, which may be produced, for example, by means of a lithographic process, a jet process similar to an ink jet printer, or even a galvanic process. Such signal lines 40 may also be produced in a multilayer technology. In any case, the signal lines should be provided in such a way that they essentially do not protrude and do not substantially impair the external geometry of the rod-shaped hollow body or the device for drainage of the brain 1. By means of the signal interface 50, the signals may then be transmitted to a measuring arrangement or a measuring system via a corresponding signal line 64 or also wirelessly. The sensor may be supplied with power in a wired or wireless manner, for example, via an inductive coupling. Alternatively, the energy that is required may also be obtained from a temperature difference between the body and the environment. According to one embodiment, the device for drainage of the brain may comprise a thermal element for this purpose. If a collection container is provided for the drained liquid and the signals are transmitted wirelessly, the entire device for drainage of the brain may be provided without interfering inlets and outlets, which makes the application considerably more comfortable.

In region A where the application is situated in a ventricle of the brain, further sensors 31, 32, 33 may also be provided, which may also be part of a second sensor arrangement 30. These sensors 31, 32, 33 may be, for example, temperature sensors, pressure sensors or oxygen saturation sensors. Although not shown in FIG. 1, these sensors may also be connected to the signal interface 50 through corresponding signal lines.

The measurement of the intracranial pressure, the cerebral blood flow and neuronal activities should be carried out according to the scheme shown in FIG. 2. The probe has an external drainage guide that extends axially down to the ventricles of the brain and serves to remove excess CSF. In the direction of the skull, this drainage is secured by a screw connection to prevent it from falling out. Additional security is provided by a locking device such as a locknut. The measuring device for pressure, temperature, oxygen saturation and brain activity is situated in regions A and B. These signals are transmitted to the outside via a cable 64 and connected to the external measuring device. In this regard, data may also be transmitted to an external measuring device via RFID, WLAN or other wireless methods.

FIG. 2 then shows the application of the device for drainage of the brain 1 to a human cranium. In the introduced and applied state, region A is situated in the area of the ventricle 5 so that the drainage openings 12 are in the area of the ventricle in order to be able to drain a liquid present there. As can be seen in FIG. 2, the sensors of the first sensor arrangement 20 are situated in the region B, which, in the applied state, lies in the area of the cerebral mass. The temperature, pressure, oxygen saturation or brain activity can be measured in this area. The sensors of the second sensor arrangement 30 are situated in the area of the ventricle in order to be able to record physical parameters at this location as well. By means of measurement signals, which are not shown in FIG. 2, the measured signals may be forwarded to a signal interface 50 in order to then be forwarded to the measurement system via a signal or data line 64. It should be understood that the measuring system may also be integrally provided on the device for drainage of the brain 1 so that no explicit signal or data line 64 is necessary.

In the region C, which is situated in the area of the cranium, the device for drainage of the brain 1 may be fixed to the cranium 2. In this way, it is possible to prevent the device for drainage of the brain 1 from shifting relative to the skull, causing the sensor arrangements to shift as well, which could potentially generate measurement errors as a result. The rod-shaped hollow body 10 and the device for drainage of the brain 1 may be attached to the cranium 2 by means of a cranial block with the cranial block 61 being locked in place on the rod-shaped hollow body 10 with a locknut 62. In addition, the device for drainage of the brain 1 may have a drainage line 63 through which drained liquid may be removed.

Figure 3:
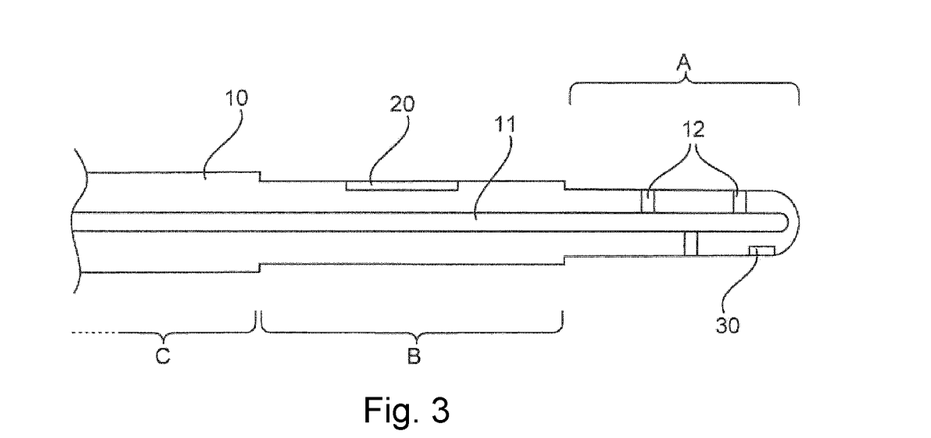
FIG. 3 shows a stepped or offset geometry of the rod-shaped hollow body according to one embodiment of the invention.
Figure 4:
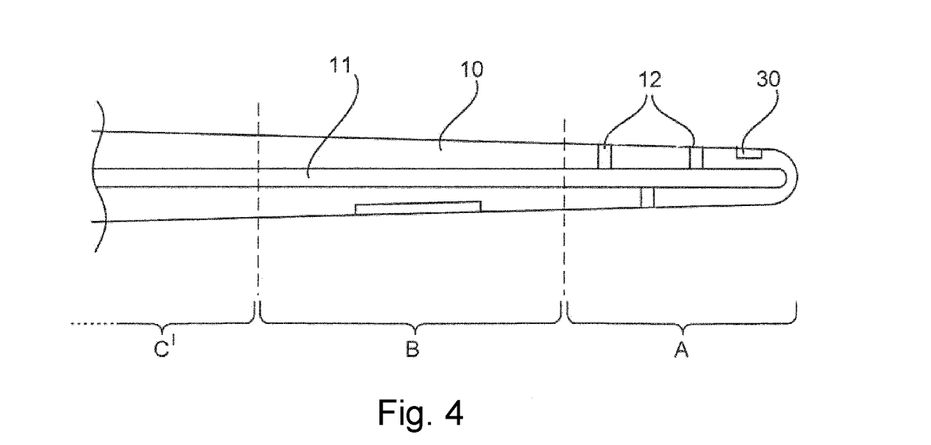
FIG. 4 shows a conical, distally tapered geometry of the rod-shaped hollow body according to one embodiment of the invention.

FIGS. 3 and 4 describe exemplary embodiments with regard to the external shape of the device for drainage of the brain 1 or the rod-shaped hollow body 10. FIG. 3 shows an embodiment in which the rod-shaped hollow body has a stepped outer geometry, which may be stepped, for example, at the points where the probable transition between the cranium 2 and the cerebral mass 4 and between the cerebral mass 4 and the ventricle 5 is expected. In other words, the steps may, for example, be between region A and region B and/or between region B and region C. As has already been described with reference to FIG. 1, the first sensor device 20 is then situated again in region B and the second sensor device 30 in the region A if said device is to be provided. The drainage openings 12 are situated here in region A. If such a stepped outer geometry of the rod-shaped hollow body 10 is provided, in particular between regions B and C, this may facilitate the attachment to the outer cranium and prevent the rod-shaped hollow body from penetrating further into the cranium. Since the anatomy of each patient is different, varying probe lengths may be kept ready-made or may be prefabricated on an individualised basis. It should be understood that such a step may also be provided exclusively between regions B and C in which case the transition between regions A and B is substantially continuous with respect to the external geometry. FIG. 4 shows a further embodiment in which the outer geometry of the rod-shaped hollow body C is conical so that no external steps are provided at this point. The position of the first and second sensor arrangement 20, 30 is analogous to FIG. 3 as is the position of the drainage openings 12. It should be understood that a hybrid geometry may also be used in which, for example, a step is provided between regions B and C while regions B and A are substantially conical or cylindrical.

FIG. 5 shows a further exemplary embodiment of the rod-shaped hollow body 10 with the inner drainage channel 11 situated therein. In the embodiment shown in FIG. 5, the rod-shaped hollow body has no drainage opening in the frontal area so that such an embodiment may possibly causes fewer injuries. The drainage opening 12 provided in the cylindrical area of region A may, for example, be round, oval or elliptical. An embodiment of the region A with only a single end-side drainage opening 12 makes it possible to keep region A short in order to also drain very flat ventricular areas. The mouth of the drainage opening 12 may have rounded corners on the outside of the rod-shaped hollow body so that any shearing of tissue during insertion may be substantially avoided. In this region A, in turn, sensors may be provided: in the embodiment shown here, for example, a pressure sensor or a temperature sensor. These sensors may be provided, for example, on the cylindrical outer wall of the region A or in the frontal area.

Figure 6:
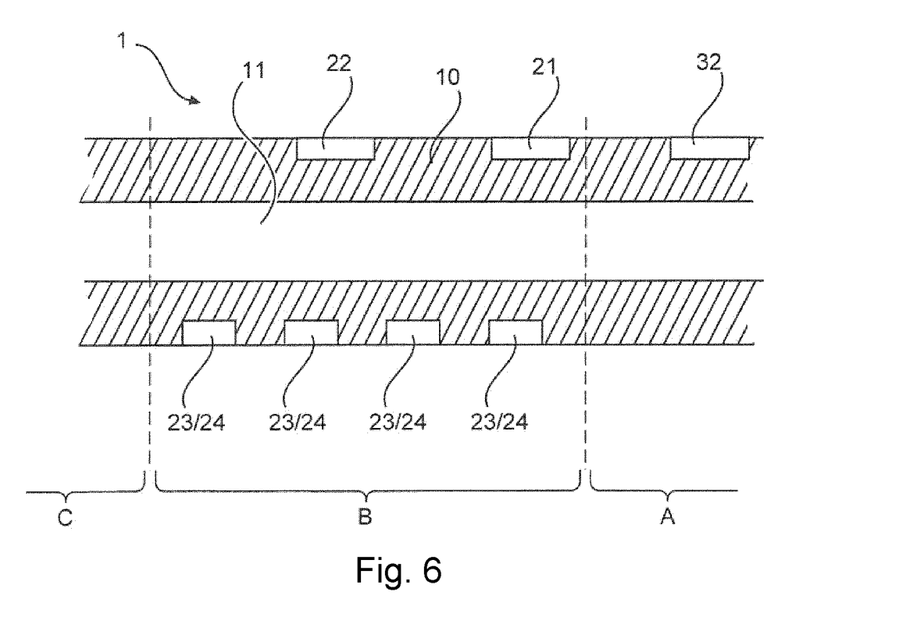
FIG. 6 shows an exemplary arrangement of a plurality of similar sensors in order to perform, for example, a spatially resolved measurement.

FIG. 6 shows a partial view of a sectional view of the device for drainage of the brain 1 in which several uniform sensors may be provided along the longitudinal extension. In this case, the sensors 23 and 24 are provided multiple times in region B so that a spatially resolved measurement can take be taken. Such a spatially resolved measurement may be, for example, a temperature measurement, an oxygen saturation measurement or a brain activity measurement. It should be understood that such multiple sensors may also be provided in region A, which is situated in the ventricular area of the brain.

Figure 7:
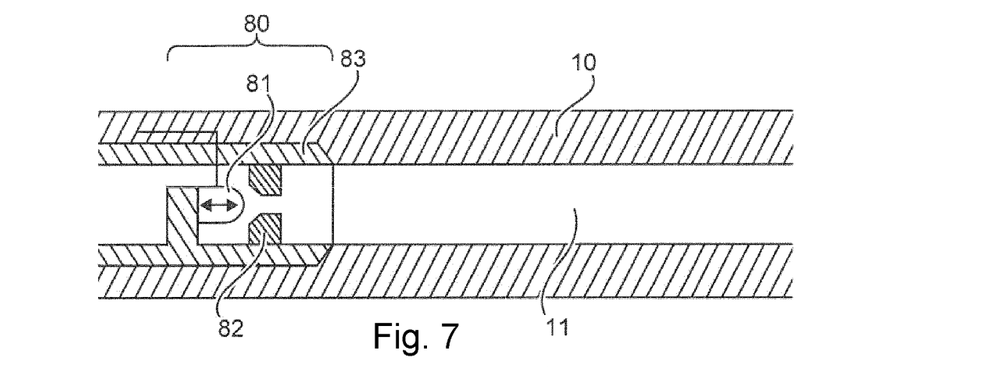
FIG. 7 shows an arrangement of a valve arrangement in the drainage channel for controlling the pressure in the ventricle.

FIG. 7 shows a sectional view of a further exemplary embodiment of the invention in which a valve arrangement 80 is provided in the interior of the rod-shaped hollow body 10. This valve arrangement may be used to control the drainage flow through the drainage channel 11. For this purpose, the valve arrangement has, for example, a valve seat 82 and a movable valve element 81. The valve seat 82 may, for example, be firmly connected to a wall 83 of the drainage channel 11. The valve element 81 may move relative to the position of the inner wall of the drainage channel 11 to sealingly engage with the valve seat 82. The valve element may be controlled so that, for example, a constant presettable pressure is created and so that the valve maintains this pressure substantially regulated. In the embodiment shown in FIG. 7, the inner wall 83 of the drainage tube is provided as a separate tube, said tube 83 being able to function as a base for a valve module, which may be prefabricated. In this case, the valve seat 82 may be fastened to such a tube 83 as well as the valve element 81 with corresponding control lines. Such a module, consisting of the elements inner tube 83, valve seat 82 and valve element 81, may be inserted into the inner drainage channel of the rod-shaped hollow body 10 as a prefabricated element during manufacture. For this purpose, the inner wall of the drainage channel 11 may have a step or a recess so that the inner wall of the tube 83 together with the remaining inner wall of the drainage channel 11 forms an aligned surface and does not have any ridges or gaps, which could possibly lead to problems with respect to sterilisation. It should be understood that such a valve device may be provided proximal to the drainage openings and may be situated both in region C and in region B or A.

Figure 8:
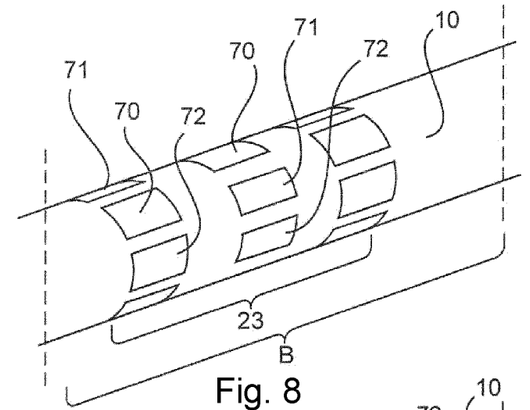
FIG. 8 shows an exemplary arrangement of an oxygen measurement/oxygen saturation sensor with one or more light sources and light sensors arranged at the same length position.

FIG. 8 shows an exemplary embodiment of the outside of the rod-shaped hollow body 10 in which the structural design is explained here by using the example of a sensor 23. In the arrangement shown in FIG. 8, the oxygen sensor has one or more light sources 70 that are able to emit light of different wavelengths. The emitted light may, for example, be in the red range or in the infrared range. Wavelengths above 570 nm or above 600 nm, for example, are preferred. Corresponding photosensitive sensors 71 and 72 are provided, which are arranged in the arrangement shown in FIG. 8 at the same height next to the light source 70. The first photosensitive sensor 71 is a light sensor that is sensitive to a first wavelength of the light source 70 while the second light sensor 72 is a sensor that responds to a second different wavelength. In this way, different parameters in the oxygen saturation may be measured due to different wavelength. It should be understood that a plurality of such arrangements consisting of a light source 70 and two light sensors 71 and 72 may be provided as shown in FIG. 8. It should be understood that such a sensor arrangement is not limited to the three rings as shown in FIG. 8. The two light sensors 71 and 72 may also be realised in a single component.

Figure 9:
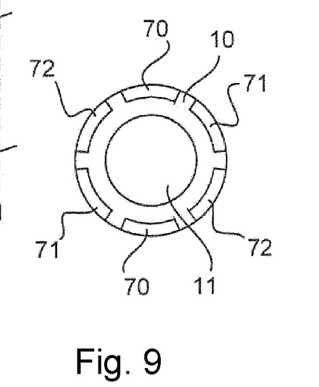
FIG. 9 shows a sectional view of the arrangement of FIG. 8 with a sectional view through the sensor rim.

Corresponding thereto, FIG. 9 shows a sectional view through the rod-shaped hollow body 10 with the drainage channel 11 situated therein. In turn, the light source 70 and the first photosensitive sensor 71 and the second photosensitive sensor 72 are arranged along the circumference. In the arrangement shown in FIG. 9, two light sources, two first photosensitive sensors and two second photosensitive sensors are provided along the circumference, which are arranged in alternation, that in each case a first and a second photosensitive sensor 71, 72 is adjacent to the light source 70. It should be understood that such an arrangement may also include, for example, a light source 70 and a first photosensitive sensor 71 and a photosensitive sensor 72 each along the circumference.

Figure 10:
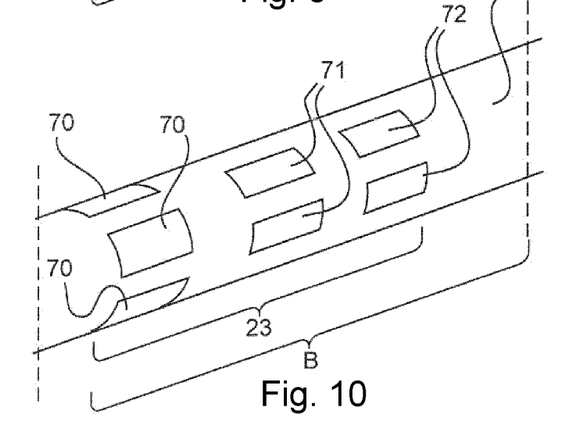
FIG. 10 shows an exemplary arrangement of an oxygen measurement/oxygen saturation sensor with one or more light sources and light sensors arranged at spaced length positions.

FIG. 10 shows a further embodiment of the invention in which one or more light sources 70 are arranged at one height while the photosensitive sensors 71 and 72 are spaced from them in the longitudinal direction. It should be understood that also a plurality of first sensors and second sensors may be distributed along the circumference and that the light source 70 may be arranged in the middle between the first photosensitive sensor and the second photosensitive sensor 71, 72.

Figure 11:
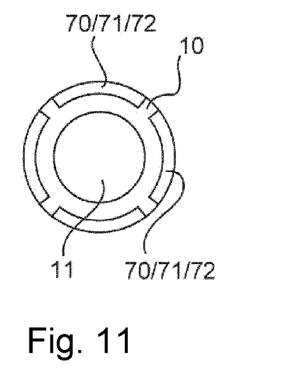
FIG. 11 shows a sectional view of the arrangement of FIG. 10 with a sectional view through the sensor rim in which essentially only one type of sensor/light source is arranged in each rim.

Corresponding to FIG. 10, FIG. 11 shows a sectional view of the rod-shaped hollow body 10 with the inner drainage channel 11 situated therein in which only one type of sensor or the light source is arranged in a sectional plane through the sensors.

The sensors shown in FIGS. 8 to 11 may be embedded in a recess or a plurality of recesses 13 provided in the outer wall of the rod-shaped hollow body 10 so that these sensors and light sources do not protrude beyond the outer surface of the remaining rod-shaped hollow body. The light source 70 may be controlled by the measuring system and, for example, be actuated continuously or operated in a pulsed manner. It should be understood that the sensors for detecting the light with different wavelengths may also detect a plurality of different wavelengths and that a plurality of such sensors can also form a corresponding detection array so that, due to the local distribution and the light intensities detected there with corresponding wavelengths, conclusions may be drawn, for example, about an oxygen saturation. In particular, punctiform light sources and also substantially punctiform sensors as well as sectoral light sources and sensors may be used.

In addition, sensors for detecting brain activity may also be provided in a geometry similar to that in FIGS. 8 and 10 as well as 9 and 11. Such sensors can detect the potential difference between one another, i.e. between different sensors, as well as with respect to an external reference potential. The electrodes can have the same sized surfaces but also have differently sized surfaces and geometry depending on the desired application. It should be understood that such electrodes and sensors may also be produced with print technology according to the printing methods referenced above. The provision of such electrodes for measuring brain activity has the significant advantage over electrodes, which are usually placed on the outside of the cranium, in that they measure directly at the site of brain activity development and have no signal loss or distortions through the cranium. Such an electrode arrangement for detecting brain activity is also usually provided in region B of the rod-shaped hollow body, which is situated in the area of the brain mass 4.

In addition, it should be noted that the term "comprising" does not exclude other elements or steps, and that the term "one" or "a" does not exclude a plurality. It must further be noted that features described with reference to any of the embodiments above may also be used in combination with other features or steps of other embodiments described above. Reference signs in the claims are not to be considered a restriction.

LIST OF REFERENCE SIGNS

A First region/ventricular area
B Second region/cerebral mass area
C Third region/skullcap area
1 Device for drainage of the brain
2 Skullcap
3 Brain
4 Cerebral mass
5 Ventricle
9 Measuring system
10 Rod-shaped hollow body
11 Inner drainage channel of the rod-shaped hollow body
12 Drainage opening/drainage opening arrangement
13 Depression/recess for receiving a sensor/sensors
20 First sensor arrangement
21 Sensor/temperature sensor of the first sensor arrangement
22 Sensor/pressure sensor of the first sensor arrangement
23 Sensor/oxygen saturation sensor of the first sensor arrangement
24 Sensor/brain activity sensor of the first sensor arrangement
30 Second sensor arrangement
31 Sensor/temperature sensor of the second sensor arrangement 32 Sensor/pressure sensor of the second sensor arrangement
33 Sensor/oxygen saturation sensor of the second sensor
40 Signal connection
50 Signal interface
61 Cranial block
62 Locknut of the cranial block
63 Drainage line
64 Signal/data line
70 Light source of the oxygen saturation sensor
71 First light sensor of the oxygen saturation sensor
72 Second light sensor of the oxygen saturation sensor
80 Controllable valve arrangement
81 Valve element
82 Valve seat
83 Valve section of the inner wall of the drainage channel

The invention claimed is:

1. A brain drainage device for a brain, the brain drainage device comprising:
   a rod-shaped hollow body with an inner drainage channel for insertion through a cranium into the brain, wherein the rod-shaped hollow body has a first region that is designed to protrude into a ventricle situated in the brain and a second region that is arranged proximally from the first region, wherein the second region is designed to lie in a cerebral mass in the brain;
   a drainage opening arrangement connected to the inner drainage channel through which liquid can be drained from the ventricle into the inner drainage channel;
   a first sensor arrangement with at least one sensor for measuring a physical parameter, wherein the first sensor arrangement is arranged in the second region to measure a physical parameter of the cerebral mass and,
   a signal interface connected to the first sensor arrangement to transmit measurement data determined by the first sensor arrangement to a measuring system,
   wherein the drainage channel extends proximally to the drainage opening arrangement and comprises a controllable valve arrangement for selectively opening and closing the drainage channel in response to a pressure sensed by the first sensor arrangement, and
   wherein the controllable valve arrangement comprises a valve seat connected to an inner wall of the drainage channel and a valve element that is displaceable with respect to the drainage channel and that is sealing relative to the valve seat.

2. The device of claim 1, wherein the at least one sensor includes an oxygen content sensor, a pressure sensor, a temperature sensor, or a brain activity sensor.

3. The device of claim 1, further comprising a second sensor arrangement with at least one sensor that includes at least one of an oxygen content sensor, a pressure sensor, or a temperature sensor, for determining a corresponding physical parameter in the ventricle, wherein the second sensor arrangement is connected to the signal interface to transmit measurement data determined by the second sensor arrangement to the measuring system.

4. The device of claim 3, wherein the at least one sensor of the first sensor arrangement or the at least one sensor of the second sensor arrangement is configured to detect an oxygen content or an oxygen saturation in the cerebral mass or the ventricle and comprises at least one light source configured to emit light having at least a first wavelength and a second wavelength, and a first light sensor associated with the light source and sensitive to the first wavelength and a second light sensor associated with the light source and sensitive to the second wavelength.

5. The device of claim 4, wherein the first light sensor is arranged axially or azimuthally spaced from the at least one light source and the second light sensor is arranged axially or azimuthally spaced from the at least one light source.

6. The device of claim 1, wherein the drainage opening arrangement forms at least one of an oval or elliptical opening.

7. The device of claim 1, wherein a portion of the inner wall of the drainage channel, the valve seat, and the valve element are formed as a preassembled unit, which can be introduced into the rod-shaped hollow body during manufacture.

8. The device of claim 1, further comprising a third region disposed proximal to the second region, wherein the third region is adapted to attach the device for drainage of the brain to a cranium.

9. The device of claim 1, wherein the first sensor arrangement comprises at least one sensor for measuring temperature, brain pressure, oxygen content, or brain activity, wherein the at least one sensor extends longitudinally along the rod-shaped hollow body to perform a spatially resolved measurement along the rod-shaped hollow body.

10. The device of claim 1, wherein the rod-shaped hollow body has at least one recess in the first region or in the second region and, wherein the first or second sensor arrangement is flush with a surface in the recess.

11. The device of claim 1, wherein a signal connection between the first sensor arrangement and the signal interface is a signal connection produced by printing technology.

12. The device of claim 1, wherein the at least one of the sensor of the first sensor arrangement is a sensor produced by printing technology.

13. The device of claim 1, wherein the rod-shaped hollow body is made of a magnetically inactive material.

* * * * *